United States Patent
Shin et al.

(10) Patent No.: US 12,376,833 B2
(45) Date of Patent: Aug. 5, 2025

(54) METHODS AND SYSTEMS FOR RANDOM NOISE SUPRESSION AND FILTERING OF ACOUSTIC CLUTTER VIA AUTOREGRESSIVE MOVING AVERAGE FILTER

(71) Applicant: KONINKLIJKE PHILIPS N.V., Eindhoven (NL)

(72) Inventors: Jun Seob Shin, Medford, MA (US); Francois Guy Gerard Marie Vignon, Andover, MA (US); Jean-luc Francois-Marie Robert, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 488 days.

(21) Appl. No.: 16/649,319

(22) PCT Filed: Sep. 25, 2018

(86) PCT No.: PCT/EP2018/075843
§ 371 (c)(1),
(2) Date: Mar. 20, 2020

(87) PCT Pub. No.: WO2019/057981
PCT Pub. Date: Mar. 28, 2019

(65) Prior Publication Data
US 2020/0261061 A1    Aug. 20, 2020

Related U.S. Application Data

(60) Provisional application No. 62/562,544, filed on Sep. 25, 2017.

(51) Int. Cl.
A61B 8/00 (2006.01)
A61B 8/08 (2006.01)
(Continued)

(52) U.S. Cl.
CPC ........ *A61B 8/5269* (2013.01); *G01S 7/52046* (2013.01); *G01S 7/52077* (2013.01); *G01S 15/8915* (2013.01); *A61B 8/0883* (2013.01)

(58) Field of Classification Search
CPC ................ A61B 8/5269; A61B 8/0883; A61B 2034/2063; A61B 5/7203; G01S 7/52046;
(Continued)

(56) References Cited

U.S. PATENT DOCUMENTS 4,542,744 A    9/1985 Barnes et al.
4,719,923 A    1/1988 Hartwell et al.
(Continued)

OTHER PUBLICATIONS

International Search Report and Written Opinion for International Application No. PCT/EP2018/075843, filed Sep. 25, 2018, 17 pages.
(Continued)

*Primary Examiner* — Serkan Akar

(57) ABSTRACT

Systems and methods for suppressing random noise, acoustic clutter, and/or reverberation clutter in ultrasound images are disclosed. An autoregressive moving average (ARMA) filtering technique that includes generating a predictive error filter and estimating noise in ultrasound channel data is disclosed. Time-space and frequency-space ARMA filtering techniques are disclosed. An ultrasound imaging system capable of implementing the ARMA filtering techniques is disclosed.

16 Claims, 7 Drawing Sheets

(51) Int. Cl.
*G01S 7/52* (2006.01)
*G01S 15/89* (2006.01)

(58) Field of Classification Search
CPC ............. G01S 7/52077; G01S 15/8915; G06T 2207/10132; G06T 5/002
See application file for complete search history.

(56) References Cited

U.S. PATENT DOCUMENTS

| | | | |
|---|---|---|---|
| 5,228,009 | A | 7/1993 | Forestieri et al. |
| 6,524,249 | B2 | 2/2003 | Moehring et al. |
| 6,689,064 | B2 | 2/2004 | Hager et al. |
| 7,570,063 | B2 | 8/2009 | Van Veen et al. |
| 7,803,116 | B2 | 9/2010 | Sikdar et al. |
| 8,647,275 | B2 | 2/2014 | Sato et al. |
| 2010/0113926 | A1* | 5/2010 | Rigby ................... A61B 8/488 600/437 |
| 2014/0222361 | A1* | 8/2014 | Sheng ................... G06F 3/0346 702/96 |
| 2014/0371594 | A1* | 12/2014 | Flynn ..................... A61B 8/06 600/454 |
| 2018/0275258 | A1* | 9/2018 | Pintoffl ................... G06T 7/11 |
| 2019/0046161 | A1* | 2/2019 | Mansour .............. A61B 8/4494 |

OTHER PUBLICATIONS

Shin, et al., "Spatial Prediction Filtering of Acoustic Clutter and Random Noise in Medical Ultrasound Imaging", IEEE Transactions on Medical Imaging, vol. 36, No. 2, Feb. 2017, pp. 396-406.

Sacchi, et al., "FX ARMA Filters", SEG Expanded Abstracts, pp. 1-4. (Abstract).

Jensen, J., "Estimation of Pulses in Ultrasound B-Scan Images", IEEE Transactions on Medical Imaging, vol. 10, No. 2, Jun. 1991, pp. 164-172.

* cited by examiner

METHODS AND SYSTEMS FOR RANDOM NOISE SUPRESSION AND FILTERING OF ACOUSTIC CLUTTER VIA AUTOREGRESSIVE MOVING AVERAGE FILTER

RELATED APPLICATIONS

This application is the U.S. National Phase application under 35 U.S.C. § 371 of International Application No. PCT/EP2018/075843, filed on Sep. 25, 2018, which claims the benefit of and priority to U.S. Provisional No. 62/562,544 filed Sep. 25, 2017, which is incorporated by reference herein.

TECHNICAL FIELD

This application is directed to autoregressive-moving average (ARMA) spatial filtering. Specifically, this application is directed to ARMA spatial filtering of ultrasound channel data.

BACKGROUND

In medical ultrasound imaging, image contrast is often compromised as a result of acoustic clutter due to off-axis scattering, reverberation clutter due to near-field anatomical structures, and random electronic noise. Several techniques have been proposed in the literature to address these issues. The techniques can be broadly categorized into two main groups: 1) Coherence-based adaptive weighting and 2) Adaptive beamforming.

Adaptive weighting techniques such as the coherence factor (CF), the generalized coherence factor (GCF), the phase coherence factor (PCF) and the short-lag spatial coherence (SLSC) all require access to per-channel data to compute a weighting mask to be multiplied to the image. With apodization-based adaptive weighting methods, such as the dual apodization with cross-correlation (DAX) and its variants, weighting masks can be computed without having access to the per-channel data and hence, hardware implementation of these methods may be slightly easier. However, all adaptive weighting methods operate by weighting down the conventional image with a weighting mask. This may lead to problems such as reduced image brightness, removal of anatomical detail, and increased speckle variance.

Adaptive beamforming techniques such as the minimum variance (MV) beamforming typically involve adaptively calculating the complex apodization values from the channel data such that only mainlobe signals are passed and off-axis signals are rejected. However, MV beamforming is developed mainly for spatial resolution improvement. Currently, MV beamforming is not effective in suppressing reverberation clutter, which is often correlated with the mainlobe signals. In many cases, reverberation clutter is the dominant source of image quality degradation in vivo. Furthermore, MV beamforming is highly sensitive to phase aberration, element directivity, and signal-to-noise ratio. MV beamforming is also known to produce artifacts in speckle.

SUMMARY

The systems, methods, and/or apparatuses described herein may improve image contrast with a spatial filtering technique based on autoregressive-moving average (ARMA) model. Generally, this technique adaptively computes a spatial predictive error filter (PEF) from channel data (a previous unknown from ARMA) and then estimates and subtracts an additive noise sequence that contains contributions from off-axis clutter, reverberation clutter, and/or random noise. This technique may filter out undesirable signals that contribute to reduced image contrast directly from the ultrasound channel data. In order to filter out the undesirable signals, noise may be treated as a sequence of random innovations instead of an additive process.

ARMA modeling of radio frequency (RF) signals from the channel data results in an eigenvalue problem. A prediction error filter (PEF) may be computed from Eigen decomposition of a covariance matrix of noisy channel data. The PEF may be applied to the noisy channel data to estimate a noise sequence (e.g. any data not modeled by the RF signals). The estimated noise sequence may be subtracted from the original channel data. The remaining signal may be "clean" data that may be used to generate an ultrasound image which may have improved contrast compared to the original channel data. The ARMA process described may be repeated one or more times on the resulting clean data, which may further improve the resulting image.

According to an exemplary embodiment of the disclosure, a method may include acquiring ultrasound channel data, generating a predictive error filter with an autoregressive moving average model, estimating, with the predictive error filter, noise in the ultrasound channel data, and subtracting the noise from the ultrasound channel data to obtain clean channel data. Estimating the predictive error filter with the autoregressive moving average model may include generating a multi-order model of the predictive error filter, converting the multi-order model and the ultrasound channel data to matrix form, solving an eigenvalue problem for the predictive error filter, wherein the eigenvalue problem comprises a correlation matrix of a noisy sequence times the predictive error matrix equal to a variance of noise times the predictive error matrix, wherein a solution of the eigenvalue problem for the predictive error filter is an eigenvector corresponding to a minimum eigenvalue of the correlation matrix of the noisy sequence. Estimating the noise in the ultrasound channel data may include deconvolving the predictive error filter and the noisy sequence.

According to an exemplary embodiment of the disclosure, an ultrasound imaging system may include an ultrasound transducer array configured to transmit and receive ultrasound signals, at least one channel operatively coupled to the ultrasound transducer configured to transmit channel data based, at least in part, on the received ultrasound signals, and a signal processor operatively coupled to the at least one channel, wherein the signal processor may be configured to acquire the channel data from the at least one channel, generate a predictive error filter with an autoregressive moving average model, estimate, with the predictive error filter, noise in the channel data, and subtract the noise from the channel data to obtain clean channel data.

According to a further exemplary embodiment of the disclosure, a method may include acquiring beamsum data, the beamsum data responsive to a plurality of ultrasound transmit events in a plurality of directions, generating a predictive error filter with an autoregressive moving average model, estimating, with the predictive error filter, noise in the beamsum data, and subtracting the noise from the beamsum data to generate clean data.

DETAILED DESCRIPTION

Figure 1:
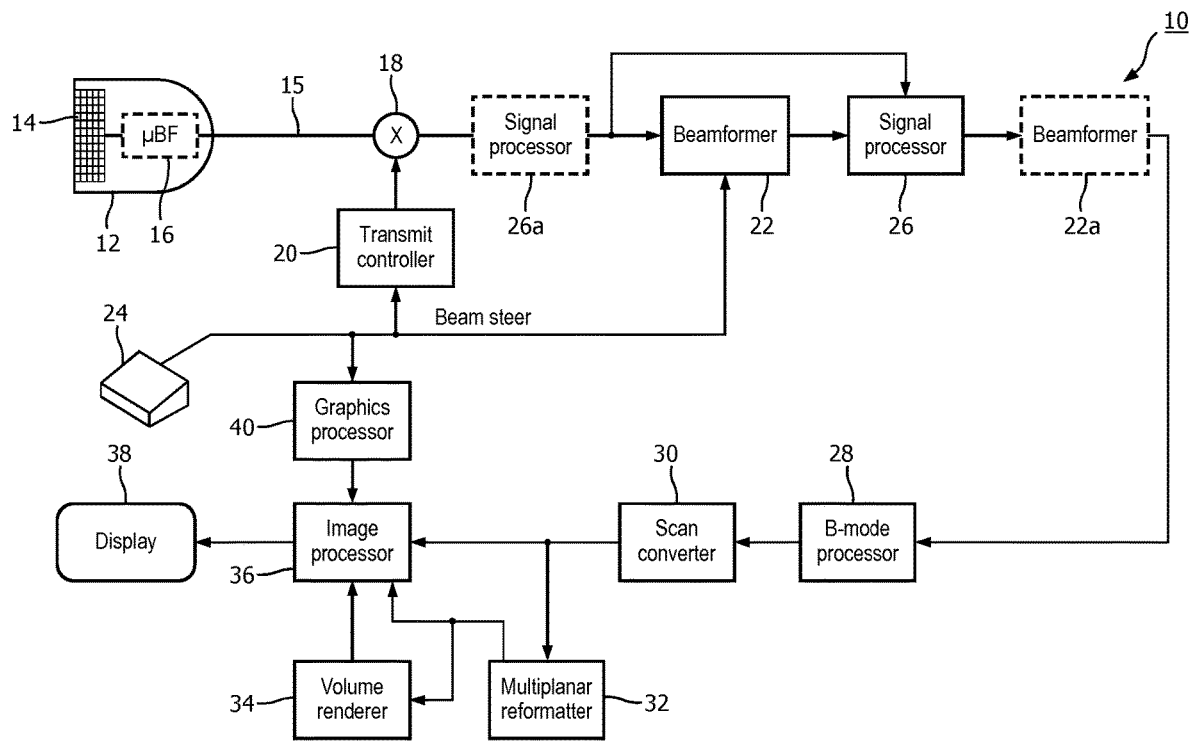
FIG. 1 is a block diagram of an ultrasound imaging system according to principles of the present disclosure.

The following description of exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system.

The following detailed description is therefore not to be taken in a limiting sense, and the scope of the present system is defined only by the appended claims. The leading digit(s) of the reference numbers in the figures herein typically correspond to the figure number, with the exception that identical components which appear in multiple figures are identified by the same reference numbers. Moreover, for the purpose of clarity, detailed descriptions of certain features will not be discussed when they would be apparent to those with skill in the art so as not to obscure the description of the present system.

Recently, a spatial filtering technique based on autoregressive (AR) model was introduced in medical ultrasound. The AR model is described in detail in "Spatial prediction filtering of acoustic clutter and random noise in medical ultrasound imaging," J. Shin and L. Huang, Transactions on Medical Imaging, 2016, which is herein incorporated by reference in its entirety. However, the AR model-based filtering technique described by Shin and Huang converts an autoregressive-moving-average (ARMA) problem into an AR problem and applies linear prediction. The AR technique minimizes the prediction error energy to find a solution to a problem where both the prediction error filter (PEF) and the noise are unknowns. Thus, the technique of Shin and Huang may lead to inaccurate signal modelling and hence, a suboptimal performance.

According to principles of the disclosure, to overcome at least some of the shortcomings of the AR technique, a spatial filtering technique based on an ARMA model is applied which may suppress random noise, acoustic clutter, and/or reverberation clutter to enhance image contrast. This technique adaptively computes a spatial PEF from ultrasound channel data, and then estimates and subtracts the estimated noise sequence that contains contributions from off-axis clutter, reverberation clutter and/or random noise.

The ARMA filtering technique (or simply ARMA method) described herein is distinct from the adaptive weighting and adaptive beamforming techniques described in the background of the disclosure. For example, the ARMA filtering technique does not use weighting masks for pixel-by-pixel weighting of the original image, and the ARMA filtering technique does not adaptively compute the complex apodization values to form an image. Rather, the ARMA filtering technique filters out undesirable signals that may contribute to reduced image contrast directly from ultrasound channel data.

Briefly, the ARMA filtering technique described herein allows signals received from a given direction, which may appear as "linear events" immersed in noise in the time-space (T-X) domain (e.g., aperture domain), may be properly represented by means of an ARMA model. In the method described herein, the noise is treated as a sequence of random innovations instead of an additive process.

ARMA modelling of ultrasound channel radio frequency (RF) signals may result in an eigenvalue problem in which a PEF may be computed from Eigen-decomposition of a covariance matrix of the original, noisy channel data. The computed PEF may be applied to the noisy channel data to estimate a colored (e.g., non-white noise) noise sequence from which an additive noise sequence is estimated. The additive noise sequence may include all the signals that are not modelled by the ARMA model, for example, random noise, off-axis clutter, and/or reverberation clutter. The estimated additive noise sequence may be subtracted from the original, noisy channel data to yield "clean" data. The clean data may be used to form an ultrasound image. The clean data may be used as an input into an iterative ARMA model. That is, the ARMA filtering technique described may be performed multiple times to yield clean data.

An ultrasound imaging system capable of performing the ARMA filtering technique according principles of the current disclosure may include an ultrasound transducer array configured to transmit and receive ultrasound signals and at least one channel operatively coupled to the ultrasound transducer configured to transmit channel data based, at least in part, on the receive ultrasound signals. The ultrasound imaging system may further include a signal processor operatively coupled to the channel. The signal processor may be configured to acquire the at least one channel data from the channel, generate a PEF with an ARMA model, estimate, with the PEF, noise in the channel data, and subtract the noise from the ultrasound data to obtain clean channel data.

Referring to FIG. 1, an ultrasound imaging system 10 constructed in accordance with the principles of the present disclosure is shown in block diagram form. In the ultrasonic diagnostic imaging system of FIG. 1, an ultrasound probe 12 includes a transducer array 14 for transmitting ultrasonic waves and receiving echo information. A variety of transducer arrays are well known in the art, e.g., linear arrays, convex arrays or phased arrays. The transducer array 14, for example, can include a two dimensional array (as shown) of transducer elements capable of scanning in both elevation and azimuth dimensions for 2D and/or 3D imaging. The transducer elements of transducer array 14 may be coupled via channels 15 to a microbeamformer 16 in the probe 12 in some embodiments. A separate channel may be provided for each transducer element of the transducer array 14 or for each patch of transducer elements. However, for clarity of the diagram, only one line is illustrated for the channels 15 in FIG. 1. The microbeamformer 16 may control transmission and reception of signals by the transducer elements in the array. In this example, the microbeamformer 16 is coupled by the probe cable to a transmit/receive (T/R) switch 18, which switches between transmission and reception and protects the main beamformer 22 from high energy transmit signals. In some embodiments, the T/R switch 18 and other elements in the system can be included in the transducer probe rather than in a separate ultrasound system base. The transmission of ultrasonic beams from the transducer array 14 under control of the microbeamformer 16 is directed by the transmit controller 20 coupled to the T/R switch 18 and the beamformer 22, which receives input from the user's operation of the user interface or control panel 24. One of the functions controlled by the transmit controller 20 is the direction in which beams are steered. Beams may be steered straight ahead from (orthogonal to) the transducer array, or at different angles for a wider field of view. The partially beamformed signals produced by the microbeamformer 16 are coupled to a main beamformer 22 where partially beamformed signals from individual patches of transducer elements are combined into a fully beamformed signal.

In some embodiments, the microbeamformer 16 is omitted. The transmit controller 20 may control the transducer array 14 directly through the T/R switch 18. Data from the transducer array 14 elements may be transmitted via channels 15 to the main beamformer 22.

The beamformed signals are coupled to a signal processor 26. The signal processor 26 can process the received echo signals in various ways, such as bandpass filtering, decimation, I and Q component separation, and harmonic signal separation. The signal processor 26 may also perform additional signal enhancement such as speckle reduction, signal compounding, and noise elimination. The signal processor 26 may be implemented in hardware (e.g., Application Specific Integrated Circuit (ASIC)), software, or a combination thereof.

As shown in FIG. 1, in some embodiments, the signal processor 26 may receive ultrasound signals from the channels 15 prior to beamforming by beamformer 22. For example, the signal processor 26 may apply the ARMA filtering technique described above to the signals from the channels 15 (e.g., channel data). In some embodiments, the beamformer 22 may provide appropriate delays and/or geometrical alignment to each channel 15, and signal processing may be performed by the signal processor 26 prior to summing of the channel signals. In some embodiments, the signal processor 26 may perform the ARMA filtering technique on the channel data and receive commands from the beamformer 22 for summing of the channel signals. The signal processor 26 may apply any desired and/or required summations prior to providing the signals to the B-mode processor 28.

In some embodiments, as shown by block 22a in dashed lines in FIG. 1, beamformer 22 may be implemented as two units, one for providing appropriate delays and/or geometrical alignment and another unit may be included for providing summing and/or other combining of channel data if necessary. In some embodiments, microbeamformer 16 may provide delays and/or geometrical alignment to the channels 15 and the beamformer 22 may be implemented after the signal processor 26 to provide summing and/or other combining of channel data. In some embodiments, as shown by blocks 26a in dashed lines in FIG. 1, signal processor 26 may be implemented as multiple units. For example, a first signal processor may be implemented prior to beamformer 22 to perform signal processing directly to the channel data, and a second signal processor may be implemented after the beamformer 22 for additional processing (e.g., bandpass filtering).

Alternatively, in the context of plane wave imaging (PWI) or diverging wave imaging (DWI), the ARMA filtering technique may be implemented in the transmit beamspace domain rather than in the channel domain. In PWI/DWI, a broad transmit beam in the form of either a plane wave or a diverging wave is emitted in a particular direction by the transducer array 14 and all scan lines (e.g. beamsum signals) may be generated using the received per-channel data via a delay-and-sum (DAS) beamforming approach performed by the beamformer 22 and/or microbeamformer 16. This may result in the acquisition by the ultrasound imaging system 10 of a low quality ultrasound image, but the image maybe acquired with a single transmit event. In PWI/DWI, such a process may be repeated for multiple transmit directions and the beamsum signals obtained from each transmit direction may be coherently compounded to produce a high quality ultrasound image. In some pre-existing ultrasound imaging systems, this version of the ARMA filtering technique may be easier to implement.

Continuing the description of the elements of FIG. 1, the processed signals are coupled to a B mode processor 28, which can employ amplitude detection for the imaging of structures in the body. The signals produced by the B mode processor are coupled to a scan converter 30 and a multiplanar reformatter 32. The scan converter 30 arranges the echo signals in the spatial relationship from which they were received in a desired image format. For instance, the scan converter 30 may arrange the echo signal into a two dimensional (2D) sector-shaped format, or a pyramidal three dimensional (3D) image. The multiplanar reformatter 32 can convert echoes which are received from points in a common plane in a volumetric region of the body into an ultrasonic image of that plane, as described in U.S. Pat. No. 6,443,896 (Detmer). A volume renderer 34 converts the echo signals of a 3D data set into a projected 3D image as viewed from a given reference point, e.g., as described in U.S. Pat. No. 6,530,885 (Entrekin et al.) The 2D or 3D images are coupled from the scan converter 30, multiplanar reformatter 32, and volume renderer 34 to an image processor 36 for further enhancement, buffering and temporary storage for display on an image display 38. The graphics processor 40 can generate graphic overlays for display with the ultrasound images. These graphic overlays can contain, e.g., standard identifying information such as patient name, date and time of the image, imaging parameters, and the like. For these purposes the graphics processor receives input from the user interface 24, such as a typed patient name. The user interface can also be coupled to the multiplanar reformatter 32 for selection and control of a display of multiple multiplanar reformatted (MPR) images.

Returning to the ARMA filtering technique, a method according to principles of the present disclosure may include acquiring ultrasound channel data as described above, generating a predictive error filter with an autoregressive moving average model, estimating, with the predictive error filter, noise in the ultrasound channel data, and subtracting the noise from the ultrasound channel data to obtain clean channel data.

Estimating the predictive error filter with the autoregressive moving average model may include generating a multi-order model of the predictive error filter, converting the multi-order model and the ultrasound channel data to matrix form, and solving an eigenvalue problem for the predictive error filter. As described in more detail below, the eigenvalue problem may include a correlation matrix of a noisy sequence times the predictive error matrix equal to a variance of noise times the predictive error matrix, and a solution of the eigenvalue problem for the predictive error filter is an eigenvector corresponding to a minimum eigenvalue of the correlation matrix of the noisy sequence. After the PEF has been generated, estimating the noise in the ultrasound channel data may include deconvolving the PEF and the noisy sequence.

Expanding the brief explanation of the ARMA filtering technique above in more mathematical detail, a linear (or a linear phased) array (e.g., transducer array 14 of FIG. 1) may have a pitch g and a linear event with slope $\psi$ in the per-channel data domain (or the T-X domain). The $(x+1)^{th}$ channel signal $s_t(x+1)$ for this array can be described as:

$$s_t(x+1) = s_{t-xg\psi}(1) \qquad \text{Equation (1)}$$

Wherein the maximum value of x is based on the number of channels.

Applying Fourier transforms to both sides of Equation (1), the following equation is obtained:

$$S_f(x+1) = S_f(1)e^{-i2\pi f x g \psi} \qquad \text{Equation (2)}$$

Where f is the temporal frequency, e is the Euler's number. The time shift in the time-space (T-X) domain shown in Equation (1) becomes a phase shift in the frequency-space (F-X) domain as shown in Equation (2). For each temporal frequency $f_0$ over the bandwidth of the transducer, Equation (2) may be expressed as an autoregressive (AR) model:

$$S_{f0}(x+1) = a_{f0}(1) S_{f0}(x) \qquad \text{Equation (3)}$$

For an AR model of order 4 (e.g., p=4), the model becomes:

$$S_{f0}(x+1) = a_{f0}(1) S_{f0}(x) + a_{f0}(2) S_{f0}(x-1) + \ldots + a_{f0}(p) S_{f0}(x+1-p) \qquad \text{Equation (4)}$$

Where p denotes the number of filter coefficients and determines the dominant spatial frequency components. A lower value of p (e.g., p=1) results in a more aggressive filter. A higher value of p (e.g., p=6) results in a less aggressive filter. A filter that is too aggressive may result in artifacts in the final image, whereas a less aggressive filter may allow in so much noise that image contrast is not improved. The inventors found that the value of p may be empirically selected based, at least in part, on applying the method multiple times with different values of p and selecting the value of p that provides the best image quality. For some medical ultrasound imaging applications, a value of p equal to or about 4 may provide images with improved contrast with minimal filter artifacts.

Returning to the ARMA filtering technique, Equation (4) in prediction error form is:

$$\Sigma_{k=0}^{p} g_{f0}(k) S_{f0}(x-k+1) = 0 \qquad \text{Equation (5)}$$

Where $g_{f0}(0) = 1$ and $g_{f0}(k) = -a_{f0}(k)$, k=1, . . . , p.

If noise is added, Equation (5) becomes:

$$Y_{f0}(x) = S_{f0}(X) + W(x) \qquad \text{Equation (6)}$$

Where W(x) is the random white noise sequence and $Y_{f0}(x)$ is the noisy sequence for the temporal frequency $f_0$. Substituting $S_{f0}(x-k+1) = Y_{f0}(x-k+1) - W(x-k+1)$ in Equation (5), results in:

$$\Sigma_{k=0}^{p} g_{f0}(k) Y_{f0}(x-k+1) = \Sigma_{k=0}^{p} g_{f0}(k) W(x-k+1) = E(x+1) \qquad \text{Equation (7)}$$

Where E is error, and $\Sigma_{k=0}^{p} g_{f0}(k) W(x-k+1)$ is a non-white innovation noise sequence (i.e. colored noise). Equation (7) in matrix form with the subscript $f_0$ omitted is:

$$Yg = Wg = e \qquad \text{Equation (8)}$$

Where Y is the convolution matrix of the noisy sequence $Y_{f0}(x)$, W is the convolution matrix of the noise sequence $W_{f0}(x)$, g is the matrix form of the prediction error filter (PEF), and e is the error matrix.

If zero-mean white noise that is spatially uncorrelated with signal is assumed, the PEF, g, can be estimated by transforming Equation 8 into the following eigenvalue problem of the form $Av = \lambda v$:

$$Y^H Y g = Y^H W g \qquad \text{Equation (9)}$$

$$R_Y g = \sigma w^2 g \qquad \text{Equation (10)}$$

Where H is the conjugate transpose operator, $R_Y$ is the correlation matrix of the noisy sequence (e.g., $R_Y = Y^H Y$), and $\sigma w^2$ is the variance of the noise.

The desired PEF is the eigenvector corresponding to the minimum eigenvalue of $R_Y$. Therefore the PEF, g may be estimated. The minimum eigenvalue is an estimate of the noise variance $\sigma w^2$. An estimate $\hat{W}(x)$, the normalization of the colored noise sequence, can be obtained by deconvolving the PEF from the non-white noise innovation term:

$$Gy = Gw = e \qquad \text{Equation (11)}$$

Where G is the convolution matrix of the PEF g, y is the noisy sequence, and w is the additive noise sequence.

Formulating a constrained minimization problem:

$$\min_w \| G(y-w)^H G(y-w) \|_2^2 \qquad \text{Equation (12)}$$

Equation 12 is subject to the condition:

$$w^H w = \sigma w^2 \qquad \text{Equation (13)}$$

The solution for $\hat{w}$, the normalization of the additive noise sequence, in the above minimization problem is:

$$\hat{w} = (G^H G + \mu I)^{-1} G^H G y \qquad \text{Equation (14)}$$

Where I is the identity matrix and $\mu$ is a diagonal loading factor that controls the weight given to the identity matrix. From Equation 14, the estimated noise sequence $\hat{w}$ can then be subtracted from the noisy sequence y to yield clean data g:

$$\hat{s} = y - \hat{w} = [I - (G^H G + \mu I)^{-1} G^H G] y \qquad \text{Equation (15)}$$

Note that the equation above yields $\hat{w} = y$, that is $\hat{s} = 0$, when $\mu = 0$ and $\hat{w} = 0$. Furthermore, $\hat{s} = y$ when $\mu \gg 0$. Therefore an appropriate value for $\mu$ should be selected. Similar to p in Equation 4, $\mu$ may be selected empirically. For some medical ultrasound imaging applications a value equal to or about 0.01 may be used for p. In the examples provided in the present disclosure, $\mu = 0.01$ was used.

The above eigenvalue problem was solved for $f_0$. The same problem is solved for each temporal frequency and/or temporal frequency bin over the bandwidth of the transducer array. Once the "clean" signal $\hat{s}$ is obtained for each temporal frequency and/or frequency bin, the inverse Fourier transform may be applied to transform the clean signals from the F-X domain to the T-X domain. Prior to applying the inverse Fourier transform, $\hat{s}$ for each temporal frequency may be fed back into Equation 3 for S, if desired, resulting in "cleaner" signal $\hat{s}'$. The process may be repeated more than once (e.g., 2, 3, 5 times).

The steps of the ARMA filtering technique described thus far are applied to data from an axial segment of predetermined size (e.g., a single depth of the ultrasound scan). The steps are repeated for all desired depths of the ultrasound scan.

Figure 2:
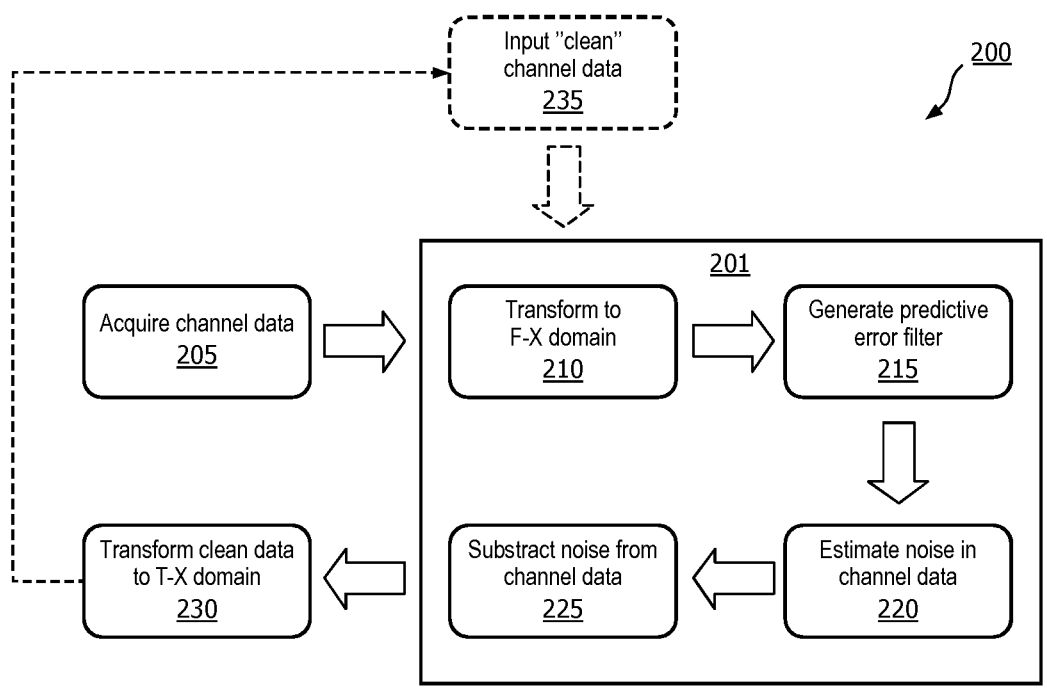
FIG. 2 is a flow chart of a method according to principles of the present disclosure.

FIG. 2 is a flowchart 200 of a method according to principles of the present disclosure. Flowchart 200 summarizes the steps of the ARMA filtering technique described mathematically above. The method illustrated in flowchart 200 is performed at a single depth (e.g., axial segment) of the ultrasound scan. The entire method of flowchart 200 (except Step 235, as explained below) may be repeated for all depths and/or desired depths of the ultrasound scan. The ARMA filtering technique may be performed at least in part by a signal processor, for example, signal processor 26 in FIG. 1. Ultrasound channel data is acquired at Step 205. As discussed in reference to FIG. 1, the channel data may be acquired by the signal processor after delays and/or geometric alignment have been applied to the channel data but prior to signal summation. At Step 210, the channel data is converted from the time-space (T-X) domain to the frequency domain (F-X) (e.g., Fourier transform). A predictive error filter (PEF) is generated at Step 215. The PEF may be generated by the method described above in reference to Equations 5-9. Once the PEF has been generated, the noise in the channel data may be estimated at Step 220. The noise may be estimated by the method described above in reference to Equations 10-13. The noise may then be subtracted from the channel data at Step 225 to obtain the "clean" data.

Steps 210-225 are performed on a single temporal frequency and/or temporal frequency bin. Accordingly, as illustrated by box 201, Steps 210-225 are repeated for each temporal frequency and/or temporal frequency bin. After Steps 210-225 have been performed for all temporal frequencies and/or temporal frequency bins, the "clean" data is converted from the F-X domain back to the T-X domain (e.g., inverse Fourier transform) at Step 230.

Once method 200 has been completed for all depths, Steps 205-230 of method 200 may be repeated for all depths by substituting the "clean" channel data from Step 230 for the originally acquired channel data from Step 205 if desired. Method 200 is then repeated for each depth of the "clean" channel data. The resulting "cleaner" channel data may then be fed back into Step 235 for another iteration, and so on. The number of iterations may be set by a user (e.g., via a user interface such as user interface 24 in FIG. 1) and/or determined by an ultrasound imaging system (e.g., ultrasound imaging system 10 in FIG. 1). In some embodiments, the ultrasound imaging system may determine the number of iterations based on a desired level of contrast, imaging application, signal-to-noise ratio, and/or other factors (e.g., probe type, T-X or F-X ARMA filtering technique used, default setting).

The equations and FIG. 2 above describe transforming from the time-space (T-X) domain to the frequency-space (F-X) domain and back again. However, it is possible to apply the ARMA filtering technique directly in the aperture or the T-X domain without having to transform the channel data to F-X domain. For example, Steps 210 and 230 of the method illustrated in flowchart 200 in FIG. 2 may be omitted. This may increase the efficiency of the method and reduce the computational burden in some applications. The T-X domain method of the ARMA filtering technique could be applied to the aperture-domain analytic signal depth-by-depth. This may allow for a reduction of the computational burden as computation does not need to be performed at individual temporal frequencies. The T-X domain method of the ARMA filtering technique may lead to results that are similar to or slightly less accurate than the F-X domain method of the ARMA filtering technique because the current ARMA modelling framework is formulated based on a narrowband assumption, and the subdivision into each temporal frequency and/or frequency bin in the F-X domain method may yield a more accurate estimation of the PEF and the noise sequence. However, the gains in computation time of the T-X method may be preferential to the more accurate results of the F-X method in some applications. Similar to the F-X method, the T-X method may also be applied iteratively if desired to maximize image contrast enhancement.

As discussed previously in reference to FIG. 1, the proposed ARMA filtering technique summarized in FIG. 2 may be implemented with plane wave imaging (PWI) or diverging wave imaging (DWI) applications. The ARMA filtering technique may be directly applied to beamsum signals obtained from different directions. For example, in PWI/DWI, the dataset may be stored in a 3D matrix of size [# of axial samples x # of scanlines x # of PW/DW transmits] as opposed to [# of axial samples x # of scanlines x # of channels] in the case of focused transmit imaging methods. Instead of applying the ARMA filtering technique at all depths in the channel domain for every scanline, the technique may be applied at all depths in the PW/DW transmit domain for every scanline in PWI/DWI. This may increase the ease of implementation on some existing ultrasound systems as access to per-channel data may be limited in some systems.

FIGS. 3-7 show example images generated by conventional techniques and the ARMA filtering technique according to principles of the present disclosure. Images generated by the ARMA filtering technique may be provided on a display of an ultrasound imaging system (e.g., display 38 in FIG. 1). Images may also be stored to a computer readable medium and/or provided to another display (e.g., a personal computer for post-exam review). The examples described below are illustrative and should not be interpreted to limit the implementations or applications of the ARMA filtering technique to the examples disclosed herein.

Figure 3:
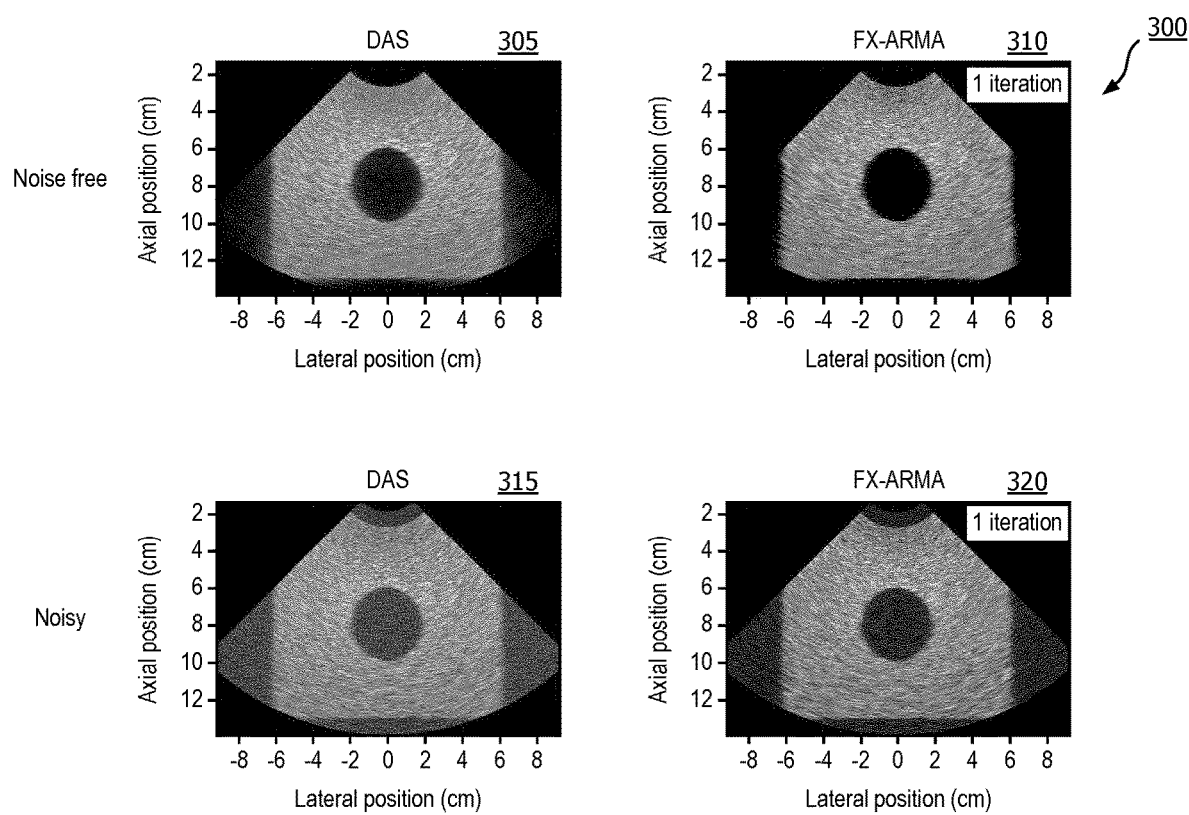
FIG. 3 shows exemplary images of a simulated phantom generated by typical methods and generated by methods according to principles of the present disclosure.

FIG. 3 shows images 300 of a simulated phantom containing a 40 mm-diameter anechoic cyst lesion. The images were simulated for a 64-element P4-2 phased array. All images are shown on a 60 dB dynamic range. Image 305 was generated using standard delay-and-sum (DAS) beamforming. Image 310 was generated using the frequency-space domain (F-X) ARMA filtering technique according to principles of the present disclosure. The F-X ARMA filtering technique was performed once. That is, the process was not repeated with the resulting clean data. Both images 305 and 310 were acquired in the absence of random noise. Comparing images 305 and 310, F-X ARMA filtering suppresses off-axis clutter and yields enhanced image contrast. Image 315 was generated using standard DAS beamforming and image 320 was generated using F-X ARMA. In images 315 and 320, random noise was present in the channel data. Comparing images 315 and 320, F-X ARMA filtering suppresses both random noise and off-axis clutter and yields enhanced image contrast.

Figure 4:
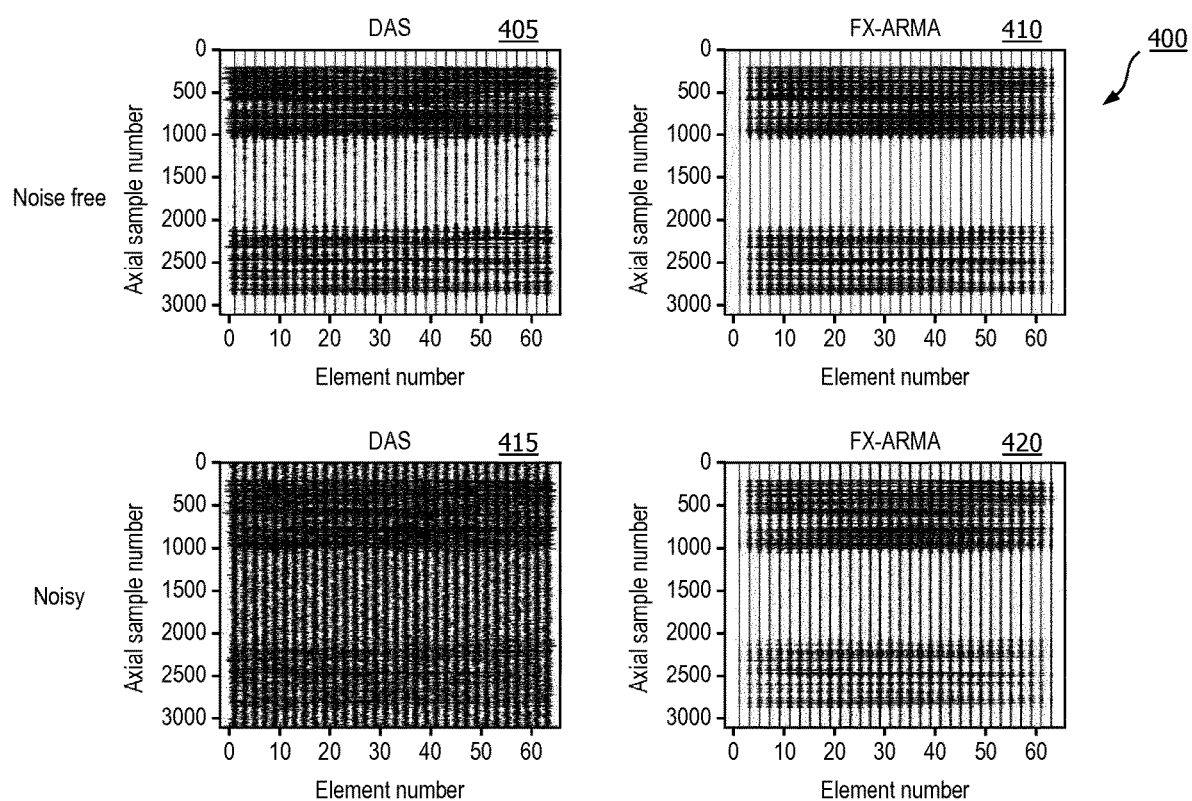
FIG. 4 shows channel data of the images shown in FIG. 3.

FIG. 4 shows post-processing channel RF data 400 taken from the center scan line (e.g., 0° steering angle) from the images 300 shown in FIG. 3. Image 405 is the channel data for image 305; image 410 is the channel data for image 310; image 415 is the channel data for image 315; and image 420 is the channel data for image 320. Every other channel signal is displayed for clearer visualization. Axial samples from sample number 1000 to 2100 correspond to the anechoic cyst lesion shown in images 300. In the absence of random noise, image 405 generated using DAS displays small-amplitude off-axis clutter signals. In contrast, image 410 illustrates that the F-X ARMA filtering suppresses much of these off-axis clutter signals while preserving most of the signals in the speckle region (e.g., outside of 1000~2100 sample region). In the presence of random noise, comparing DAS image 415 and F-X ARMA image 420, the F-X ARMA filtering provides better suppression of both the random noise and the acoustic clutter contributions from the channel RF data.

Figure 5:
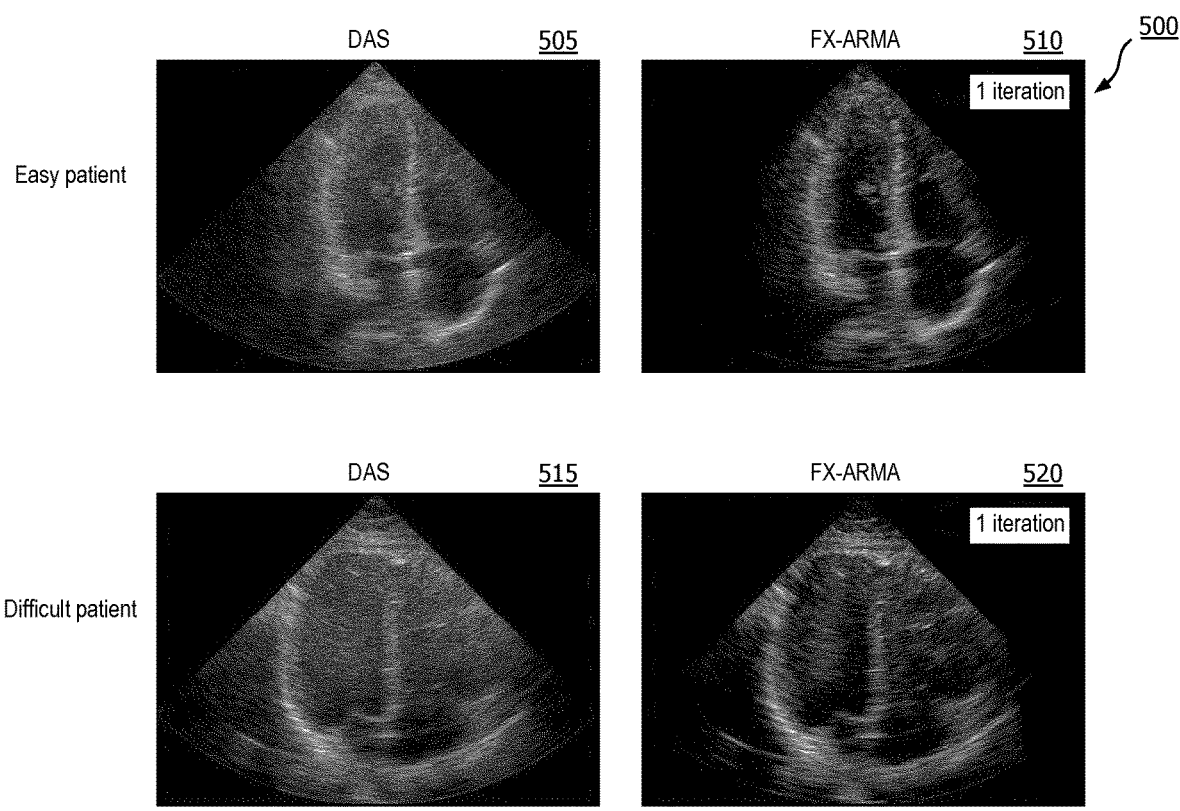
FIG. 5 shows exemplary images of hearts of patients generated by typical methods and generated by methods according to principles of the present disclosure.

FIG. 5 shows images 500 of an apical 4-chamber view of a heart. All images are shown on a 60 dB dynamic range. Images 505 and 510 were acquired from an "easy" patient. Images 515 and 520 were acquired from a "difficult" patient. Easy patients have less noisy images than difficult patients. For example, in general, it is often difficult to obtain clear images from overweight patients. That is, an easy patient may be a normal weight patient and a difficult patient may be an overweight patient in some cases. Images 505 and 515 were generated using DAS and images 510 and 510 were generated using the F-X ARMA filtering technique according to principles of the present disclosure. The F-X ARMA filtering technique was performed once. That is, the process was not repeated with the resulting clean data. In both patients, image contrast is significantly reduced in the DAS images 505 and 515 due to the presence of off-axis clutter and reverberation clutter. In comparison, the FX-ARMA images 510 and 520 show a significant amount of image contrast enhancement.

As shown in FIGS. 3-5, filtering the ultrasound channel data to acquire clean data using the ARMA filtering technique may provide enhanced image contrast compared to typical image processing techniques such as DAS.

Figure 6:
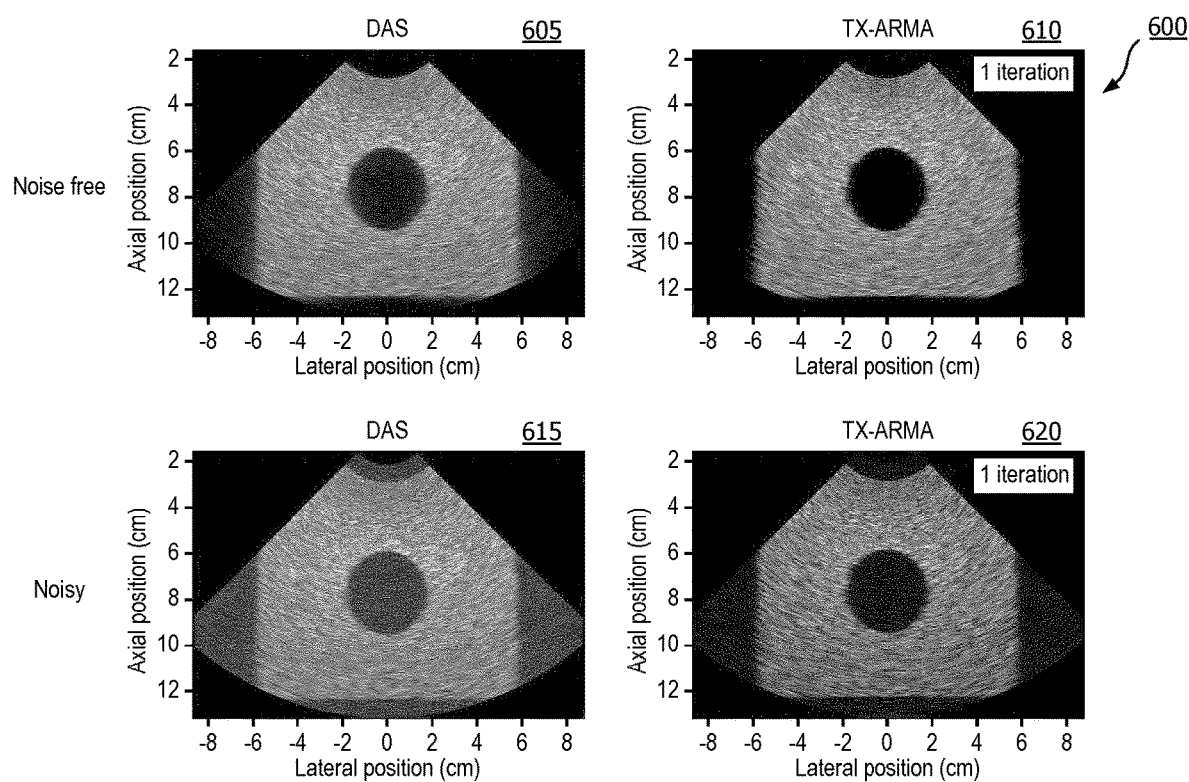
FIG. 6 shows exemplary images of a simulated phantom generated by typical methods and generated by methods according to principles of the present disclosure.

FIG. 6 shows images 600 of a simulated phantom containing a 40 mm-diameter anechoic cyst lesion. The images were simulated for a 64-element P4-2 phased array. All images are shown on a 60 dB dynamic range. Image 605 was generated using standard delay-and-sum (DAS) beamforming. Image 610 was generated using the time-space domain (T-X) ARMA filtering technique according to principles of the present disclosure. The T-X ARMA filtering technique was performed once. That is, the process was not repeated with the resulting clean data. Both images 605 and 610 were acquired in the absence of random noise. Comparing images 605 and 610, T-X ARMA filtering suppresses off-axis clutter and yields enhanced image contrast. Image 615 was generated using standard DAS beamforming and image 620 was generated using T-X ARMA. In images 615 and 620, random noise was present in the channel data. Comparing images 615 and 620, T-X ARMA filtering suppresses both random noise and off-axis clutter and yields enhanced image contrast. Although the T-X ARMA images 610 and 620 have slightly less contrast than F-X ARMA images 310 and 320 shown in FIG. 3, the T-X ARMA images still show improved contrast compared to DAS images. Thus, given the faster computation time of T-X ARMA images compared to F-X ARMA images, the T-X ARMA filtering technique may be acceptable and/or preferred in some applications.

Figure 7:
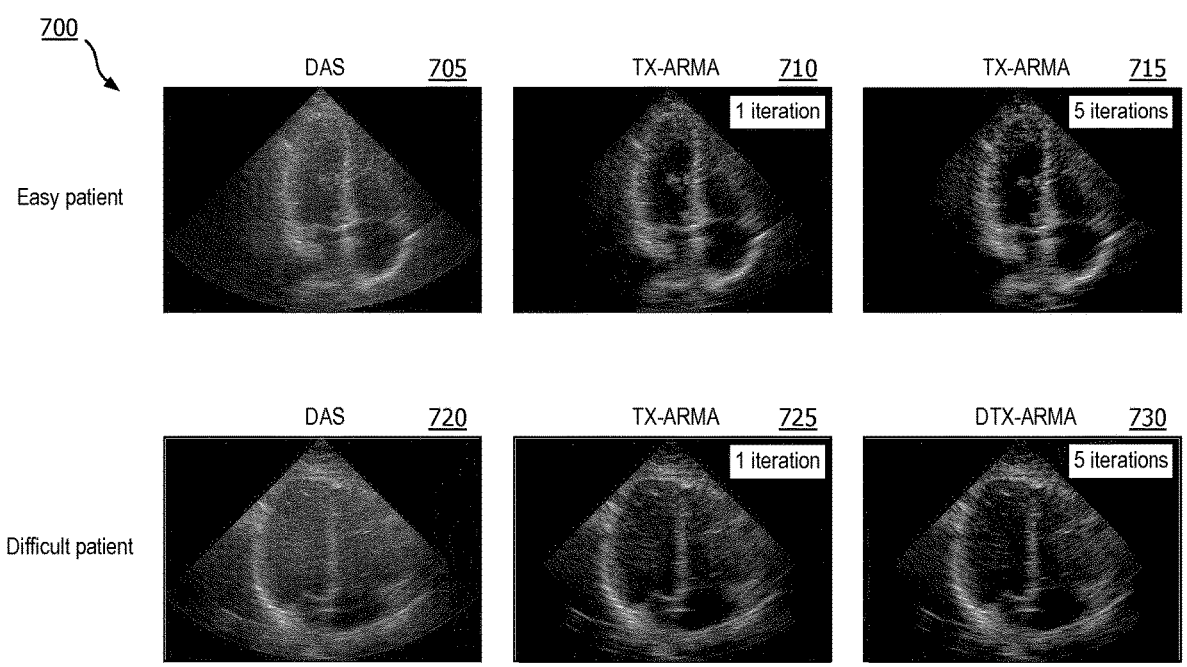
FIG. 7 shows exemplary images of hearts of patients generated by typical methods and generated by methods according to principles of the present disclosure.

FIG. 7 shows images 700 of an apical 4-chamber view of a heart. All images are shown on a 60 dB dynamic range. Images 705, 710, and 715 were acquired from an "easy" patient. Images 720, 725, and 730 were acquired from a "difficult" patient. Images 705 and 720 were generated using DAS beamforming. Images 710 and 725 were generated by applying one iteration of the T-X ARMA filtering technique. Images 715 and 730 were generated by applying five iterations of the T-X ARMA filtering technique. That is, the "clean" data from the T-X ARMA filtering technique on the first iteration was fed back into the technique four times. In the images acquired for both easy and difficult patients, image contrast is significantly reduced in the DAS images 705 and 720 due to the presence of off-axis clutter and reverberation clutter. However, a significant amount of image contrast enhancement is observed with T-X ARMA filtering for both single and multiple iterations. As shown in images 715 and 730, performing multiple iterations of T-X ARMA filtering technique may help further suppress clutter signal that remain after a single iteration of T-X ARMA filtering technique.

As shown in FIGS. 6 and 7, filtering the ultrasound channel data to acquire clean data using the ARMA filtering technique may provide enhanced image contrast compared to typical image processing techniques such as DAS, even when using the T-X ARMA method.

According to principles of the disclosure, an ARMA filtering technique (e.g., ARMA method) as described herein may be applied to ultrasound channel data to suppress random noise, acoustic clutter, and/or reverberation clutter which may enhance image contrast. This may improve a clinician's ability to locate, recognize, and/or measure anatomical features in the image. The improved contrast may improve a clinician's ability to make diagnoses based on the ultrasound image.

In various embodiments where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

Although the present system has been described with reference to an ultrasound imaging system, the present system may be extended to other imaging techniques. Additionally, the present system may be used to obtain and/or record image information related to, but not limited to renal, testicular, prostate, breast, ovarian, uterine, thyroid, hepatic, lung, musculoskeletal, splenic, nervous, cardiac, arterial and vascular systems, as well as other imaging applications related to ultrasound-guided interventions and other interventions which may be guided by real-time medical imaging. Further, the present system may also include one or more elements which may be used with non-ultrasound imaging systems with or without real-time imaging components so that they may provide features and advantages of the present system.

Further, the present methods, systems, and apparatuses may be applied to existing imaging systems such as, for example, ultrasonic imaging systems. Suitable ultrasonic imaging systems may include a Philips® ultrasound system which may, for example, support a conventional broadband linear array transducer that may be suitable for small-parts imaging.

Certain additional advantages and features of this invention may be apparent to those skilled in the art upon studying the disclosure, or may be experienced by persons employing the novel system and method of the present invention, chief of which is reduction of acoustic clutter and random noise by ultrasound imaging systems and method of operation thereof is provided. Another advantage of the present systems and method is that conventional medical imaging systems may be easily upgraded to incorporate the features and advantages of the present systems, devices, and methods.

Of course, it is to be appreciated that any one of the above embodiments or processes may be combined with one or more other embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. A method comprising:
    transmitting ultrasound waves with a transducer array of an ultrasound system;
    receiving echo information with the transducer array, the echo information responsive to the ultrasound waves;
    acquiring ultrasound channel data at a signal processor, the ultrasound channel data comprising radio frequency (RF) signals based on the echo information;
    generating a predictive error filter with an autoregressive moving average model based at least in part, on the ultrasound channel data with the signal processor, wherein generating the predictive error filter includes solving an eigenvalue problem comprising a correlation matrix of a noisy sequence times a predictive error matrix equal to a variance of noise times the predictive error matrix;
    estimating, with the predictive error filter, noise in the ultrasound channel data, wherein estimating the noise comprises;
        applying the predictive error filter to the ultrasound channel data to estimate a colored noise sequence; and
        estimating an additive noise sequence using the estimated colored noise sequence, and
        wherein the additive noise sequence includes off-axis clutter;
    subtracting the noise from the ultrasound channel data to obtain clean channel data with the signal processor, wherein generating the predictive error filter, estimating the additive noise sequence, and subtracting noise from the ultrasound channel data are performed in a time-space domain;
    iteratively performing the generating, the estimating, and the subtracting based, at least in part, on the clean channel data, wherein a number of iterations of the generating, the estimating, and the subtracting is automatically determined by the signal processor based on a desired level of contrast or a signal-to-noise ratio;
    generating image data for display based, at least in part, on the clean channel data; and
    displaying an image based on the image data.

2. The method of claim 1, wherein the method is repeated for every depth of an ultrasound scan.

3. The method of claim 1, wherein estimating the predictive error filter with the autoregressive moving average model includes:
    generating a multi-order model of the predictive error filter;
    converting the multi-order model and the ultrasound channel data to matrix form,
    wherein a solution of the eigenvalue problem for the predictive error filter is an eigenvector corresponding to a minimum eigenvalue of the correlation matrix of the noisy sequence.

4. The method of claim 3, wherein estimating the noise in the ultrasound channel data comprises deconvolving the predictive error filter and the noisy sequence.

5. The method of claim 1, further comprising geometrically aligning or applying delays to the channel data prior to generating the predictive error filter.

6. The method of claim 1, further comprising summing the clean channel data.

7. The method of claim 1, wherein estimating the noise in the ultrasound channel data includes assuming zero-mean white noise.

8. The method of claim 1, wherein the additive noise sequence includes random noise and reverberation clutter.

9. An ultrasound imaging system comprising:
    an ultrasound transducer array configured to transmit ultrasound waves and receive echo information responsive to the ultrasound waves;
    at least one channel operatively coupled to the ultrasound transducer configured to transmit channel data comprising radio frequency (RF) signals based on the echo information received by the ultrasound transducer array;
    a signal processor operatively coupled to the at least one channel, wherein the signal processor is configured to:

acquire, from the at least one channel, the channel data comprising the RF signals based on the echo information received by the ultrasound transducer array;

generate a predictive error filter with an autoregressive moving average model in a time- space domain for a number of iterations, wherein generating the predictive error filter includes solving an eigenvalue problem comprising a correlation matrix of a noisy sequence times a predictive error matrix equal to a variance of noise times the predictive error matrix;

estimate, with the predictive error filter, noise in the channel data in the time-space domain for the number of iterations, wherein estimating the noise comprises;

applying the predictive error filter to the channel data to estimate a colored noise sequence; and estimating an additive noise sequence using the estimated colored noise sequence, and wherein the additive noise sequence includes off-axis clutter; and subtract the noise from the channel data to obtain clean channel data in the time-space domain for the number of iterations, wherein the number of iterations is automatically determined based on a desired level of contrast or a signal-to-noise ratio; and an image processor configured to generate image data for display based, at least in part, on the clean channel data.

10. The ultrasound imaging system of claim 9, wherein the ultrasound transducer array includes a plurality of transducer elements and the at least one channel includes a channel for each of the plurality of transducer elements.

11. The ultrasound imaging system of claim 9, further comprising a beamformer configured to provide delays and/or geometrical alignment of the channel data, and wherein the signal processor is configured to acquire the channel data from the beamformer.

12. The ultrasound imaging system of claim 9 further comprising a display configured to display an image based on the image data.

13. A method comprising:

transmitting ultrasound waves with a transducer array of an ultrasound system, the ultrasound waves comprising a plurality of ultrasound transmit events in a plurality of directions;

receiving echo information with the transducer array, the echo information responsive to the ultrasound waves, acquiring beamsum data with a processor, wherein the beamsum data comprises radio frequency (RF) signals based on the echo information;

generating a predictive error filter with an autoregressive moving average model based, at least in part, on the beamsum data, wherein generating the predictive error filter includes solving an eigenvalue problem comprising a correlation matrix of a noisy sequence times a predictive error matrix equal to a variance of noise times the predictive error matrix:

estimating, with the predictive error filter, noise in the beamsum data, wherein estimating the noise comprises;

applying the predictive error filter to the beamsum data to estimate a colored noise sequence; and estimating an additive noise sequence using the estimated colored noise sequence, and wherein the additive noise sequence includes off-axis clutter;

subtracting the noise from the beamsum data to generate clean data, wherein generating the predictive error filter, estimating the additive noise sequence, and subtracting noise from the ultrasound channel data are performed in a time-space domain;

iteratively performing the generating, the estimating, and the subtracting based, at least in part, on the clean data, wherein a number of iterations of the generating, the estimating, and the subtracting is automatically determined by the processor based on a desired level of contrast or a signal-to-noise ratio;

generating image data for display based, at least in part, on the clean data; and displaying an image based on the image data.

14. The method of claim 13, wherein the beamsum data comprises a plurality of beamsum signals, each of the plurality of beamsum signals having a plurality of depths, and generating the predictive error filter, estimating the noise, and subtracting the noise is repeated for each of the plurality of beamsum signals for each of the plurality of depths.

15. The method of claim 13, wherein the beamsum data is generated based on coherently compounding a plurality of beamsum signals obtained from different respective beam transmit directions.

16. The method of claim 13, wherein each of the plurality of ultrasound transmit events is a plane wave or a diverging wave.

* * * * *